(12) United States Patent
Fricker et al.

(10) Patent No.: US 10,365,503 B2
(45) Date of Patent: Jul. 30, 2019

(54) METHOD IMPLEMENTED BY COMPUTER MEANS FOR CALCULATING A LENS OPTICAL SYSTEM OF A SPECTACLE OPHTHALMIC LENS FOR A WEARER

(71) Applicant: Essilor International, Charenton le Pont (FR)

(72) Inventors: Sebastien Fricker, Charenton le Pont (FR); Cyril Guilloux, Charenton le Pont (FR)

(73) Assignee: Essilor International, Charenton le Pont (FR)

( * ) Notice: Subject to any disclaimer, the term of this patent is extended or adjusted under 35 U.S.C. 154(b) by 26 days.

(21) Appl. No.: 15/533,140

(22) PCT Filed: Dec. 8, 2015

(86) PCT No.: PCT/EP2015/078926
§ 371 (c)(1),
(2) Date: Jun. 5, 2017

(87) PCT Pub. No.: WO2016/091853
PCT Pub. Date: Jun. 16, 2016

(65) Prior Publication Data
US 2017/0363883 A1   Dec. 21, 2017

(30) Foreign Application Priority Data
Dec. 8, 2014   (EP) ..................................... 14306972

(51) Int. Cl.
G02C 7/02   (2006.01)
G02C 7/06   (2006.01)
A61B 3/02   (2006.01)

(52) U.S. Cl.
CPC ............. *G02C 7/028* (2013.01); *G02C 7/024* (2013.01); *G02C 7/061* (2013.01); *A61B 3/02* (2013.01)

(58) Field of Classification Search
CPC ................................ G02C 7/024; G02C 7/028
(Continued)

(56) References Cited

U.S. PATENT DOCUMENTS 9,547,183 B2 *   1/2017   Muradore .............. G02C 7/028
2008/0273169 A1   11/2008   Blum et al.
(Continued)

FOREIGN PATENT DOCUMENTS

EP   1 884 818 A1   2/2008
EP   2 669 732 A1   12/2013
(Continued)

OTHER PUBLICATIONS

International Search Report dated Feb. 2, 2016, in PCT/EP2015/078926 filed Dec. 8, 2015.

*Primary Examiner* — Zachary W Wilkes
(74) *Attorney, Agent, or Firm* — Oblon, McClelland, Maier & Neustadt, L.L.P.

(57) ABSTRACT

A method implemented by computer means for calculating a lens optical system of a spectacle ophthalmic lens for a wearer. The method includes providing an aberration target lens fulfilling the requirements of: a first set of aberration data of the aberration target lens, a first set of wearing parameters of the aberration target lens, and a first set of lens parameters of the aberration target lens. The method further includes providing a distortion target consisting of target distortion values where the target distortion values are reduced or enhanced in at least a modified distortions zone when compared to the distortion values of the aberration target lens, and calculating the lens optical system by using (Continued)

an optimization method which jointly uses the aberration target lens and the target distortion values.

13 Claims, 11 Drawing Sheets

(58) Field of Classification Search
USPC .................................. 351/159.74–159.77
See application file for complete search history.

(56) References Cited

U.S. PATENT DOCUMENTS

| | | |
|---|---|---|
| 2009/0066912 A1 | 3/2009 | Miura |
| 2011/0007266 A1 | 1/2011 | Blum et al. |
| 2011/0043752 A1 | 2/2011 | Blum et al. |
| 2013/0335699 A1 | 12/2013 | De Rossi et al. |
| 2014/0293216 A1 | 10/2014 | Muradore et al. |
| 2015/0131056 A1 | 5/2015 | Paille et al. |

FOREIGN PATENT DOCUMENTS

| | | |
|---|---|---|
| WO | WO 2010/043704 A1 | 4/2010 |
| WO | WO 2012/119668 A1 | 9/2012 |
| WO | WO 2013/072396 A1 | 5/2013 |

\* cited by examiner

METHOD IMPLEMENTED BY COMPUTER MEANS FOR CALCULATING A LENS OPTICAL SYSTEM OF A SPECTACLE OPHTHALMIC LENS FOR A WEARER

FIELD OF THE INVENTION

The invention relates to a method for calculating an optical system by optimization.

The invention further relates to a method for manufacturing a spectacle ophthalmic lens, relates to a computer program product and also relates to a computer-readable medium.

BACKGROUND OF THE INVENTION

Optimization methods for calculating optical systems are known from the state of the art. However there is still a need for improved spectacle ophthalmic lenses so as to better fulfill viewing needs.

SUMMARY OF THE INVENTION

The inventors have noticed that a method for calculating an optical system by optimization which could be adjusted according to different parameters, such as lens parameters or wearer's parameters could provide enhanced wearer's satisfaction when taking into account aberration data for the wearer.

A problem that the invention aims to solve is to provide a lens optical system of a spectacle ophthalmic lens by simultaneously taking into account aberrations and distortions so as to fulfill viewing needs.

Thus, the present invention provides a method implemented by computer means for calculating a lens optical system (OS) of a spectacle ophthalmic lens for a wearer where the spectacle ophthalmic lens comprises a back surface and a front surface, the back surface being positioned closest to the wearer's eye when the spectacle ophthalmic lens is worn, wherein the method comprises the steps of:
  providing an aberration target lens (ATL) fulfilling the requirements of:
    a first set of aberration data of the aberration target lens (ATL) including at least an aberration datum at a point of said aberration target lens (ATL) chosen within the list consisting of a power $PPO_{ATL}$, an astigmatism amplitude value $AST_{ATL}$ with an astigmatism axis $AXE_{ATL}$ and an addition $Add_{ATL}$,
    a first set of wearing parameters of the aberration target lens (ATL), and
    a first set of lens parameters of the aberration target lens (ATL);
  providing a distortion target (DT) consisting of target distortion values where the target distortion values are reduced or enhanced in at least a modified distortions zone when compared to the distortion values of the aberration target lens (ATL);
  calculating the lens optical system (OS) by using an optimization method which jointly uses the aberration target lens and the target distortion values.

"Distortion values" are values related to deviations from rectilinear projection. A rectilinear projection is a projection in which straight lines in a scene remain straight in an image. "Distortion" thus qualifies the image deformations due to the lens and should be distinguished from aberrations causing image blur such as power error, resulting astigmatism and higher order aberrations. The wording "distortion" is unambiguously known for a person skilled in the art of spectacle ophthalmic lenses. Examples of distortions are further given within the scope of the present document.

According to the invention, one can provide an efficient target lens with distortions easy to be calculated.

According to the invention, the first set of aberration data of the aberration target lens (ATL) includes at least an aberration datum at a point of said aberration target lens (ATL) chosen within the list consisting of a power $PPO_{ATL}$, an astigmatism amplitude value $AST_{ATL}$ with an astigmatism axis $AXE_{ATL}$, and an addition $Add_{ATL}$.

According to an embodiment, the power $PPO_{ATL}$ corresponds to the optical power at the far vision control point and is substantially equal to the prescribed mean sphere $SPH_P + CYL_P/2$, the astigmatism amplitude value $AST_{ATL}$ corresponds to the astigmatism at the far vision control point and is substantially equal to the prescribed cylinder $CYL_P$ in positive cylinder convention, the astigmatism axis $AXE_{ATL}$ corresponds to the astigmatism axis at the far vision control point and is equal substantially to the prescribed axis $AXE_P$ in positive cylinder convention and the addition $Add_{ATL}$ corresponds to the difference in optical power between the near vision control point and the far vision control point, and is equal to the prescribed addition $ADD_P$.

For example, the expression "is substantially equal" used above may be illustrated as:

$$|PPO_{ATL} - (SPH_P + CYL_P/2)| < 0.25 \text{ Diopter}$$

$$|AST_{ATL} - AST_P| < 0.25 \text{ Diopter}$$

$$|AXE_{ATL} - AXE_P| < 30°$$

According to an embodiment:
  the prescribed mean sphere, the prescribed cylinder $CYL_P$, the prescribed axis $AXE_P$ are determined for a wearer when looking in far vision conditions, and the prescribed addition $ADD_P$ is the difference between the prescribed mean sphere determined for a wearer when looking in near vision conditions and the prescribed mean sphere determined for a wearer when looking in far vision conditions.

An aberration target lens (ATL) may also be provided under the form of a plurality of power values $PPO_{ATL}$, astigmatism values $AST_{ATL}$ and astigmatism axis values $AXE_{ATL}$ at various gaze directions (alpha, beta).

According to the invention, said power $PPO_{ATL}$ is provided at a point on the lens where the prescription is controlled: this point may be a far vision control point or a near vision control point.

In general, for a progressive addition lens, the point corresponds to the far vision control point and power $PPO_{ATL}$ is substantially equal to the prescribed power in far vision. For a mid-distance lens, the point corresponds to the near vision control point and power $PPO_{ATL}$ is substantially equal to the prescribed power in near vision.

According to the invention, the lens optical system (OS) is calculated by using an optimization method which jointly uses the aberration target lens and the target distortion values such as the aberration values of said ophthalmic lens are close to the aberration values of the aberration target lens (ATL) and such as the distortion values of said ophthalmic lens are close to the distortion values of the distortion target (DT).

According to an embodiment, the optical system is optimized such as to minimize the quadratic difference between the aberration values of the ophthalmic lens and the aberration values of the aberration target lens (ATL) on one hand, the quadratic difference between the distortion values of the ophthalmic lens and the distortion values of the distortion target (DT) on the other hand.

Namely, the optimization process of said embodiment minimizes the following merit function:

$$MF = W_{PPO}\sum_{i=1}^{N}(PPO_{OS}(\alpha_i, \beta_i) - PPO_{ATL}(\alpha_i, \beta_i))^2 +$$

$$W_{ASR}\sum_{i=1}^{N}(ASR_{OS}(\alpha_i, \beta_i) - ASR_{ATL}(\alpha_i, \beta_i))^2 +$$

$$W_{DIST}\sum_{i=1}^{M}(DIST_{OS}(\gamma_i, \delta_i) - DT(\gamma_i, \delta_i))^2$$

where;
$PPO_{OS}$ is the optical power of the optical system (OS)
$PPO_{ATL}$ is the optical power of the aberration target lens (ATL)
$ASR_{OS}$ is the resulting astigmatism of the optical system (OS)
$ASR_{ATL}$ is the resulting astigmatism of the aberration target lens (ATL)
$DIST_{OS}$ is the distortion value of the optical system (OS)
DT is the distortion target value of the distortion target
$(\alpha_i, \beta_i)$, from 1 to N is a mesh of gaze directions
$(\gamma_i, \delta_i)$, from 1 to M is a mesh of peripheral directions
$W_{PPO}$ is the weight of the optical power term of the merit function
$W_{ASR}$ is the weight of the resulting astigmatism term of the merit function
$W_{DIST}$ is the weight of the distortion term of the merit function According to an embodiment, the method further comprises a step consisting in providing distortion values of the aberration target lens (ATL) before the step of providing a distortion target (DT).

According to this embodiment, distortion values can be determined by calculation from a set of numerical data describing the geometry and the refractive index of the aberration target lens (ATL) and gaze direction of the said lens wearer or by a measurement of an aberration target lens (ATL).

Then, starting from such distortion values which are calculated, measured or estimated on an aberration target lens ATL, one can determine distortion values, reduced or enhanced for a distortion target DT.

However, this step consisting in providing distortion values of the aberration target lens (ATL) is optional. Indeed, for example, it is known that by considering two ophthalmic lenses which only differ by their addition values, the ophthalmic lens having the highest addition has also the enhanced distortion values. Then without requiring any evaluation of distortion values of the aberration target lens (ATL) having a given addition Add1, it is possible to be certain that another lens having a greater (respectively lower) addition Add2 has enhanced (respectively reduced) distortion values.

According to different embodiments that may be combined according to all technically possible embodiments, the method of the invention may comprise following additional features:

the average within the distortion zone of absolute difference between the distortion values of the aberration target lens and the reduced or enhanced target distortion values of the distortion target is at least 5%, preferably 10%. Said value can be determined according to the following formula.

$$\frac{\sum_{i=1}^{N}|DT(\gamma_i, \delta_i) - Dist(ATL, \gamma_i, \delta_i)|}{\sum_{i=1}^{N}|Dist(ATL, \gamma_i, \delta_i)|} \geq Q$$

where:
$(\gamma_i, \delta_i)$ is a mesh of the distortion zone
N is the number of points in the mesh
Dist is the distortion criterion
Q=5%, preferably 10%
said first set of wearing parameters of the aberration target lens (ATL) including a first distance, $d_{ATL}$, between the center of rotation of the eye of the wearer and the back surface of said aberration target lens (ATL), said first set of lens parameters of the aberration target lens (ATL) including a first refractive index, $n_{ATL}$ of said aberration target lens (ATL), a first base curvature, $B_{ATL}$, being the curvature on a reference point of the front surface of the aberration target lens (ATL), the distortion target (DT) is a distortion target lens (DTL) and said distortion target lens (DTL) is provided with a second set of aberration data, a second set of wearing parameters including a second distance, $d_{DTL}$, between a center of rotation of the eye of the wearer and the back surface of said distortion target lens (DTL), and a second set of lens parameters including a second refractive index, $n_{DTL}$ of said distortion target lens (DTL) and a second base curvature, $B_{DTL}$, and
the first and the second set of aberration data differ from at least a data value and/or the first and the second set of wearing parameters differ from at least one wearing parameter value and/or the first and the second set of lens parameters differ from at least one lens parameter value.
the following criteria are met:
the spectacle ophthalmic lens is a single vision ophthalmic lens,
the first set of aberration data comprises at least a value chosen within the list consisting of a power $PPO_{ATL}$, preferably at the optical center of said aberration target lens (ATL), an astigmatism amplitude $AST_{ATL}$, preferably at the optical center of said aberration target lens (ATL) with an astigmatism axis value $AXE_{ATL}$, with the proviso that addition $Add_{ATL}$ is nil (ATL is a single vision lens),
the second set of aberration data comprises at least a value chosen within the list consisting of a power $PPO_{DTL}=PPO_{ATL}-\Delta PPO$ at the optical center of said distortion target lens (DTL), an astigmatism amplitude $AST_{DTL}=AST_{ATL}-\Delta AST$ at the optical center of said distortion target lens with an astigmatism axis value $AXE_{DTL}$, where $\Delta PPO$ and/or $\Delta AST$ is not nil,
the following criteria are met:
$\Delta PPO$ is of the same sign as $PPO_{ATL}$ and satisfies the equation: 0.25 Diopter<$|\Delta PPO|\leq$2.0 Diopter, for example $|\Delta PPO|=1$ Diopter and/or
$\Delta AST$ is of the same sign as $AST_{ATL}$ and satisfies the equation: 0.25 Diopter<$|\Delta AST|\leq$2.0 Diopter, for example $|\Delta AST|=1$ Diopter, the following criteria are met:
the spectacle ophthalmic lens is a progressive addition lens chosen within the list consisting of a lens comprising a far vision zone, an intermediate vision zone and a near vision zone; a lens comprising an intermediate vision zone and a near vision zone; a lens comprising a far vision zone and an intermediate vision zone, wherein the first set of aberration data comprises at least a power value $PPO_{ATL}$ preferably at the far vision control point of said aberration target lens (ATL), a non-nil addition $Add_{ATL}$ and optionally an astigmatism amplitude value $AST_{ATL}$, preferably at the far vision control point of said aberration target lens (ATL) with an astigmatism axis value $AXE_{ATL}$, the second set of aberration data comprises at least a value chosen within the list consisting of a power $PPO_{DTL}=PPO_{ATL}-\Delta PPO$, preferably at the far vision control point of said distortion target lens (DTL), an addition $Add_{DTL}=Add_{ATL}-\Delta Add$ and optionally an astigmatism amplitude value $AST_{DTL}=AST_{ATL}-\Delta AST$, preferably at the far vision control point of said distortion target lens (DTL) with an astigmatism axis value $AXE_{DTL}$, where $\Delta PPO$ and/or $\Delta AST$ and/or $\Delta Add$ is not nil;

the following criteria are met:
ΔAdd is positive and satisfies the equation: 0.125 Diopter≤ΔAdd≤1.5 Diopter, for example ΔAdd=0.25 Diopter and/or ΔPPO is of the same sign as $PPO_{ATL}$ and satisfies the equation: 0.25 Diopter≤|ΔPPO|≤2.0 Diopter, for example |ΔPPO|=1 Diopter and/or ΔAST is of the same sign as $AST_{ATL}$ and satisfies the equation: 0.25 Diopter≤|ΔAST|≤2.0 Diopter, for example |ΔAST|=1 Diopter.

the second refractive index $n_{DTL}$ differs from the first refractive index, $n_{ATL}$.

the second distance, $d_{DTL}$, differs from the first distance, $d_{ATL}$.

$d_{ATL}-d_{DTL}\geq 1$ mm, preferably $d_{ATL}-d_{DTL}\geq 3$ mm.

the second base curvature, $B_{DTL}$, differs from said first base curvature, $B_{AIL}$.

$B_{DTL}-B_{AIL}\geq 1$ Diopter, preferably $B_{DTL}-B_{ATL}\geq 2$ Diopter.

According to the invention, the target distortion values of the distortion target (DT) are reduced or enhanced in at least a modified distortions zone when compared to the distortion values of the aberration target lens (ATL).

According to an embodiment, the target distortion values are reduced when compared to the distortion values of the aberration target lens (ATL), for example by providing a distortion target lens (DTL) having a reduced addition $Add_{DTL}$ when compared to the addition $Add_{ATL}$ of the aberration target lens since the distortions increase with addition.

According to another embodiment, the method comprises a step consisting of providing a distortion target lens (DTL) having an enhanced addition $Add_{DTL}$ when compared to the addition $Add_{ATL}$ of the aberration target lens since an enhanced addition provides and enhanced magnification in the near vision zone.

According to the two aforementioned embodiments, one can use the method described below for obtaining a surface having an addition Add2 from a surface having an addition Add1 (with Add2 different from Add1). Using the surface with addition Add2, one can define a distortion target lens (DTL) with reduced addition $ADD_{ATL}<ADD_{ATL}$ when Add2<Add1, or with enhanced addition $ADD_{DTL}>ADD_{ATL}$ when Add2>Add1.

Firstly, according to a point sampling $(x_{i,j}, y_{i,j})$ of a plan $(0xy)$, curvatures $(C_h, C_v, C_d)$ of a starting surface S are calculated along 3 directions of the tangent plane at a given point. These 3 directions correspond to x, y axes and to diagonal axis when a projection is applied on said directions to the $(0xy)$ plan. Then, an affine transformation is applied on the curvatures to obtain 3 new curvatures $(C'_h, C'_v, C'_d)$ $$\begin{cases} C'_h = aC_h + b \\ C'_v = aC_v + b \\ C'_d = aC_d + b \end{cases}$$

a and b are calculated from:
$SPH_{FV}$=sphere of the starting surface in far vision conditions
Add1=addition of the starting surface
Add2=desired addition
Thus:
a=Add2/Add1
b=$SPH_{FV}$(1−a)

Thirdly, curvatures $(C'_h, C'_v, C'_d)$ are integrated according to the method disclosed in U.S. Pat. No. 6,955,433.

According to another embodiment, the method comprises a step consisting of providing a distortion target lens (DTL) having a power $PPO_{DTL}$ that is reduced, in absolute value, when compared to the power $PPO_{ATL}$ of the aberration target lens (ATL) since cushion or barrel distortion increases with the absolute power value.

According to another embodiment, the method comprises a step consisting of providing a distortion target lens (DTL) having an enhanced power $PPO_{DTL}$ when compared to the power $PPO_{ATL}$ of the aberration target lens (ATL) since magnification increases with power value.

According to another embodiment, the method comprises a step consisting of providing a distortion target lens (DTL) having an astigmatism amplitude value $AST_{DTL}$ that is reduced in absolute value, when compared to the astigmatism amplitude value $AST_{ATL}$ of the aberration target lens (ATL) since image deformation increases with the astigmatism amplitude value.

According to an embodiment, both back surface and front surface of the spectacle ophthalmic lens are calculated by optimization. Such a method of optimization is described in US2012/0016644 and WO2010/043704.

In another aspect, the present invention also provides a method for manufacturing a spectacle ophthalmic lens by machining a lens blank according to the lens optical system (OS) of the invention.

In still another aspect, the present invention provides a computer program product comprising one or more stored sequence of instruction that is accessible to a processor and which, when executed by the processor, causes the processor to carry out at least the steps of the method described in the present invention.

In still another aspect, the present invention also provides a computer readable medium carrying one or more sequences of instructions of the computer program product of the present invention. Further features and advantages of the invention will appear from the following description of embodiments of the invention, given as non-limiting examples, with reference to the accompanying drawings listed hereunder.

It can be appreciated that elements in the figures are illustrated for simplicity and clarity and have not necessarily been drawn to scale.

Definitions

Following definitions are provided in the frame of the present invention:

The wordings "wearer's prescription", also called "prescription data", are known in the art. Prescription data refers to one or more data obtained for the wearer and indicating for at least an eye, preferably for each eye, a prescribed sphere $SPH_p$, and/or a prescribed astigmatism value $CYL_p$ and a prescribed axis $AXIS_p$ suitable for correcting the ametropia of each eye for the wearer and, if suitable, a prescribed addition $Add_p$ suitable for correcting the presbyopia of each of his eye.

"Spectacle ophthalmic lenses" are known in the art. According to the invention, the spectacle ophthalmic lens may be selected from single vision lens (also called monofocal or unifocal lens), multifocal lens such as for example a bifocal lens, a trifocal lens, a progressive or a degressive (mid-distance) lens. The lens may also be a lens for information glasses, wherein the lens comprises means for displaying information in front of the eye. The lens may also be suitable for sunglasses or not. Preferred lenses according to the invention are single vision lenses or progressive multifocal ophthalmic lenses. All ophthalmic lenses of the invention may be paired so as to form a pair of lenses (left eye LE, right eye RE).

Figure 1:
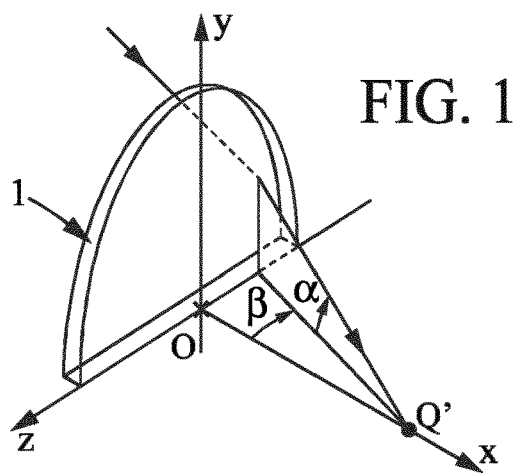
FIGS. 1 to 3 show, diagrammatically, optical systems of eye and lens and ray tracing from the center of rotation of the eye.
Figure 2:
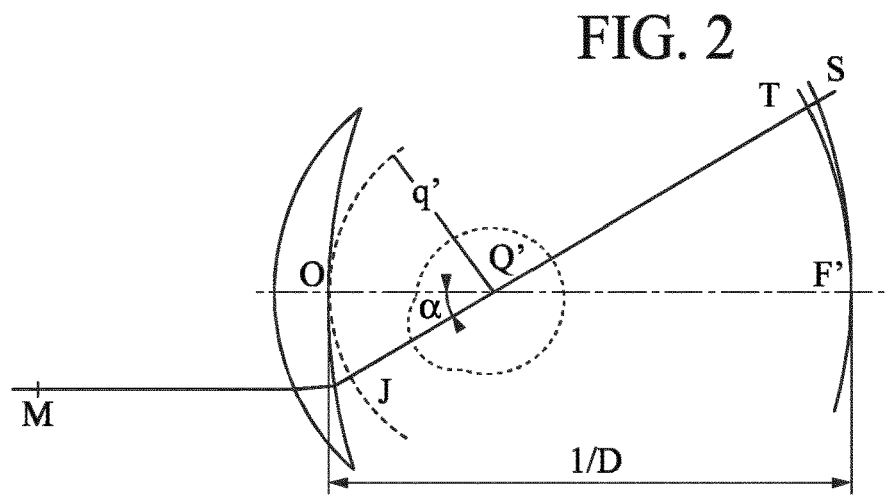

A "gaze direction" for an eye can be identified by a couple of angle values ($\alpha,\beta$), wherein said angles values are measured with regard to reference axes centered on the center of rotation of the eye. More precisely, FIG. 1 represents a perspective view of such a system illustrating parameters $\alpha$ and $\beta$ used to define a gaze direction. FIG. 2 is a view in the vertical plane parallel to the antero-posterior axis of the wearer's head and passing through the center of rotation of the eye in the case when the parameter $\beta$ is equal to 0. The center of rotation of the eye is labeled Q'. The axis Q'F', shown on FIG. 2 in a dot-dash line, is the horizontal axis passing through the center of rotation of the eye and extending in front of the wearer—that is the axis Q'F' corresponding to the primary gaze direction. This axis cuts the front surface of the lens on a point called the fitting point, which is present on lenses to enable the positioning of lenses in a frame by an optician. The fitting point corresponds to a lowering angle $\alpha$ of 0° and an azimuth angle $\beta$ of 0°. The point of intersection of the rear surface of the lens and the axis Q'F' is the point O. O can be the fitting point if it is located on the rear surface. A vertex sphere, of center Q', and of radius q', which is intercepting the rear surface of the lens in a point of the horizontal axis. As examples, a value of radius q' of 25.5 mm corresponds to a usual value and provides satisfying results when wearing the lenses.

A given gaze direction—represented by a solid line on FIG. 1—corresponds to a position of the eye in rotation around Q' and to a point J (see FIG. 2) of the vertex sphere; the angle $\beta$ is the angle formed between the axis Q'F' and the projection of the straight line Q'J on the horizontal plane comprising the axis Q'F'; this angle appears on the scheme on FIG. 1. The angle $\alpha$ is the angle formed between the axis Q'J and the projection of the straight line Q'J on the horizontal plane comprising the axis Q'F'; this angle appears on the scheme on FIGS. 1 and 2. A given gaze view thus corresponds to a point J of the vertex sphere or to a couple ($\alpha, \beta$). The more the value of the lowering gaze angle is positive, the more the gaze is lowering and the more the value is negative, the more the gaze is rising.

In a given gaze direction, the image of a point M in the object space, located at a given object distance, is formed between two points S and T corresponding to minimum and maximum distances JS and JT, which would be the sagittal and tangential local focal lengths. The image of a point in the object space at infinity is formed, at the point F'. The distance D corresponds to the rear frontal plane of the lens.

For each gaze direction ($\alpha,\beta$), a mean refractive power $Popt(\alpha,\beta)$, a module of astigmatism $Ast(\alpha,\beta)$ and an axis $Ax(\alpha,\beta)$ of this astigmatism, and a module of resulting (also called residual or unwanted) astigmatism $Asr(\alpha,\beta)$ are defined.

"Ergorama" is a function associating to each gaze direction the usual distance of an object point. Typically, in far vision following the primary gaze direction, the object point is at infinity. In near vision, following a gaze direction essentially corresponding to an angle $\alpha$ of the order of 35° and to an angle $\beta$ of the order of 5° in absolute value towards the nasal side, the object distance is of the order of 30 to 50 cm. For more details concerning a possible definition of an ergorama, U.S. Pat. No. 6,318,859 may be considered. This document describes an ergorama, its definition and its modeling method. For a method of the invention, points may be at infinity or not. Ergorama may be a function of the wearer's ametropia.

Using these elements, it is possible to define a wearer optical power and astigmatism, in each gaze direction. An object point M at an object distance given by the ergorama is considered for a gaze direction ($\alpha,\beta$). An object proximity ProxO is defined for the point M on the corresponding light ray in the object space as the inverse of the distance MJ between point M and point J of the vertex sphere:

$$ProxO = 1/MJ$$

This enables to calculate the object proximity within a thin lens approximation for all points of the vertex sphere, which is used for the determination of the ergorama. For a real lens, the object proximity can be considered as the inverse of the distance between the object point and the front surface of the lens, on the corresponding light ray.

For the same gaze direction ($\alpha,\beta$), the image of a point M having a given object proximity is formed between two points S and T which correspond respectively to minimal and maximal focal distances (which would be sagittal and tangential focal distances). The quantity ProxI is called image proximity of the point M:

$$ProxI = \frac{1}{2}\left(\frac{1}{JT} + \frac{1}{JS}\right)$$

The optical power is also called refractive power

By analogy with the case of a thin lens, it can therefore be defined, for a given gaze direction and for a given object proximity, i.e. for a point of the object space on the corresponding light ray, an optical power Popt as the sum of the image proximity and the object proximity.

$$Popt = ProxO + ProxI$$

With the same notations, an astigmatism Ast is defined for every gaze direction and for a given object proximity as:

$$Ast = \left|\frac{1}{JT} - \frac{1}{JS}\right|$$

This definition corresponds to the astigmatism of a ray beam created by the lens.

Figure 3:
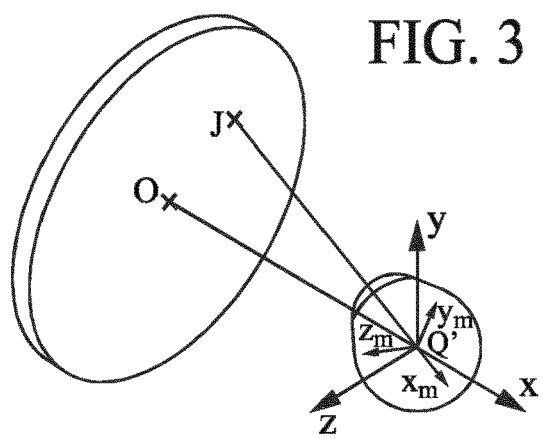

FIG. 3 represents a perspective view of a configuration wherein the parameters α and β are non-zero. The effect of rotation of the eye can thus be illustrated by showing a fixed frame {x, y, z} and a frame {$x_m$, $y_m$, $z_m$} linked to the eye. Frame {x, y, z} has its origin at the point Q'. The axis x is the axis Q'O and it is orientated from the lens towards the eye. The y axis is vertical and orientated upwardly. The z axis is such that the frame {x, y, z} is orthonormal and direct. The frame {$x_m$, $y_m$, $z_m$} is linked to the eye and its center is the point Q'. The $x_m$ axis corresponds to the gaze direction JQ'. Thus, for a primary gaze direction, the two frames {x, y, z} and {$x_m$, $y_m$, $z_m$} are the same. It is known that the properties for a lens may be expressed in several different ways and notably in surface and optically.

When referring to geometrical properties of a lens, one defines a "front surface" and a "back surface" of said lens, where the back surface is positioned on the side of the lens closest to a wearer's eye and the front surface is positioned on the opposite side of the lens when the spectacle ophthalmic lens is worn by the wearer. The front surface and the back surface geometrical characterizations, the relative geometrical spatial position of the front surface and the back surface, the refractive index of the material between said two surfaces, an ergorama and wearing conditions are data that permit calculating optical features of the lens for said given ergorama and wearing conditions.

Figure 4:
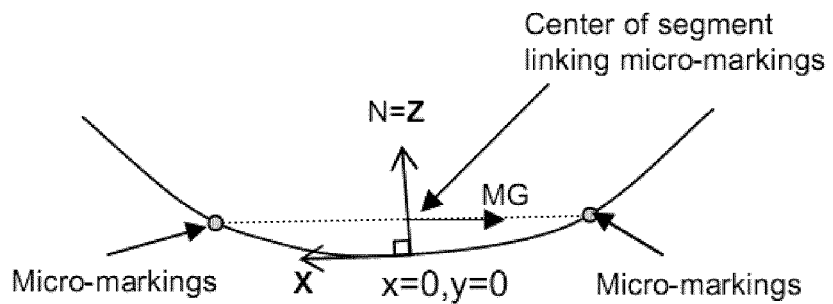
FIGS. 4 and 5 show referentials defined with respect to micro-markings, for a surface bearing micro-markings and for a surface not bearing the micro-markings respectively.
Figure 5:
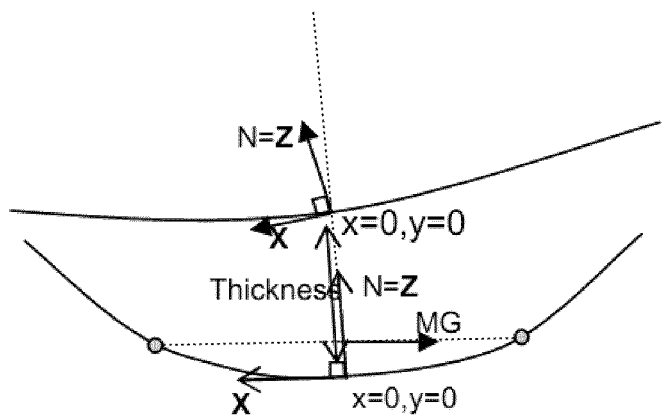

Accordingly, in the case of an ophthalmic lens, the characterization may be of a surface or optical kind. Whenever the characterization of the lens is of optical kind, it refers to the ergorama-eye-lens system described above. For simplicity, the term 'lens' is used in the description but it has to be understood as the 'ergorama-eye-lens system'. The value in surface terms can be expressed with relation to points. The points are located with the help of abscissa or ordinate in a frame as defined above with respect to FIGS. 4 and 5. The referential (x,y,z) of said figures is a direct orthonormal referential.

The values in optic terms can be expressed for gaze directions. Gaze directions are usually given by their degree of lowering and azimuth in a frame whose origin is the center of rotation of the eye. When the lens is mounted in front of the eye, a point called the fitting point (referred as FP) is placed in the front of the pupil or in the front of the eye rotation center Q' of the eye for a primary gaze direction. The primary gaze direction corresponds to the situation where a wearer is looking straight ahead. In the chosen frame, the fitting point corresponds thus to a lowering angle α of 0° and an azimuth angle β of 0° whatever surface of the lens the fitting point is positioned—rear surface or front surface.

In the remainder of the description, terms like «up», «bottom», «horizontal», «vertical», «above», «below», or other words indicating relative position may be used. These terms are to be understood in the wearing conditions of the lens.

Notably, the "upper" part of the lens corresponds to a negative lowering angle α<0° and the "lower" part of the lens corresponds to a positive lowering angle α>0°. Similarly, the "upper" part of the surface of a lens—or of a semi-finished lens blank—corresponds to a positive value along the y axis, and preferably to a value along the y axis superior to the y value corresponding to the fitting point and the "lower" part of the surface of a lens corresponds to a negative value along the y axis in the frame as defined above with respect to FIGS. 4 and 5, and preferably to a value along the y axis inferior to the y_value at the fitting point.

A "top to bottom axis" is thus defined far α varying from a maximum positive value to a most negative value when β is equal to nil. When considering the front surface and the back surface of the lens, "top to bottom axis" corresponds to the y axis.

The "meridian line" ($α_m$, $β_m$) of a progressive lens is a line defined from top to bottom of the lens and passing through the fitting point: for each lowering of the view of an angle α=$α_m$ between the gaze direction corresponding to the fitting point and the bottom of the lens, the gaze direction ($α_m$, $β_m$) is searched by ray tracing, in order to be able to see clearly the object point located in the median plane, at the distance determined by the ergorama. For each raising of the view of an angle α=$α_m$ between the gaze direction corresponding to the fitting point and the top of the lens, ($α_m$, $β_m$)=($α_m$, 0). The median plane is the median plane of the head, preferentially passing through the base of the nose. This plane may also be passing through the middle of right and left eye rotation centers.

Thus, all the gaze directions defined in that way form the meridian line of the ergorama-eye-lens system. For personalization purpose, postural data of the wearer, such as angle and position of the head in the environment, might be taken into account to determine the object position. For instance, the object position might be positioned out of median plane to model a wearer lateral shift in near vision.

The meridian line of the lens represents the locus of mean gaze directions of a wearer when he is looking from far vision to near vision.

The meridian line is usually contained in a vertical plane above the fitting point, and deflected towards the nasal side below the fitting point.

The "meridian line" of a single vision (monofocal) lens is defined as the vertical straight line passing through the optical center, OC, of the lens, where the "optical center" is the intersection of the optical axis, OA, with the front surface of a lens; the optical center, OC, thus corresponds to ($α_{OC}$, $β_{OC}$)=(0,0).

The "surface meridian line" 32 of a lens surface is defined as follow: each gaze direction ($α_m$, $β_m$) belonging to the meridian line of the lens intersects in wearing conditions the surface in a point ($x_m$, $y_m$) according to ray tracing. The surface meridian line is the set of points corresponding to the gaze directions of the meridian line of the lens.

Figure 6:
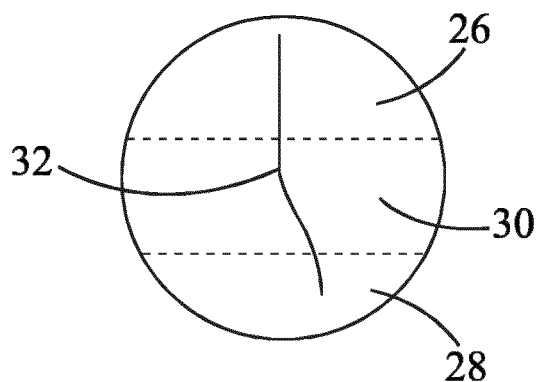
FIG. 6 shows field vision zones of a lens.

The "visual field zones" seen through a progressive lens are known to the skilled person and are schematically illustrated in FIG. 6. The lens comprises a far vision (distant vision) zone 26 located in the upper part of the lens, a near vision zone 28 located in the lower part of the lens and an intermediate zone 30 situated between the far vision zone 26 and the near vision zone 28. The lens also has a surface meridian line 32 belonging for example to the front surface and passing through the three zones and defining a nasal side and a temporal side.

A "far-vision gaze direction" is defined for a lens, as the vision gaze direction corresponding to the far vision (distant) reference point, referred as FVP, and thus ($\alpha_{FV}$, $\beta_{FV}$), where the refractive power is substantially equal to the prescribed power in far vision. It may also be defined as the gaze direction corresponding to the fitting point, FP, in which case $\alpha=\beta=0°$. Within the present disclosure, far-vision is also referred to as distant-vision.

"Astigmatism" refers to astigmatism generated by the lens, or to residual astigmatism (resulting astigmatism) which corresponds to the difference between the prescribed astigmatism (wearer astigmatism) and the lens-generated astigmatism; in each case, with regards to amplitude or both amplitude and axis;

"Micro-markings" also called "alignment reference marking" have been made mandatory on progressive lenses by the harmonized standards ISO 13666:2012 ("Alignment reference marking: permanent markings provided by the manufacturer to establish the horizontal alignment of the lens or lens blank, or to re-establish other reference points") and ISO 8990-2 ("Permanent marking: the lens has to provide at least following permanent markings: alignment reference markings comprising two markings distant from 34 mm one of each other, equidistant from a vertical plane passing through the fitting point or the prism reference point"). Micro-markings that are defined the same way are also usually made on complex surfaces, such as on a front surface of a lens with a front surface comprising a progressive or regressive front surface.

"Temporary markings" may also be applied on at least one of the two surfaces of the lens, indicating positions of control points (reference points) on the lens, such as a control point for far-vision, a control point for near-vision, a prism reference point and a fitting point for instance. The prism reference point PRP is considered here at the midpoint of the straight segment which connects the micro-markings. If the temporary markings are absent or have been erased, it is always possible for a skilled person to position the control points on the lens by using a mounting chart and the permanent micro-markings. Similarly, on a semi-finished lens blank, standard ISO 10322-2 requires micro-markings to be applied. The centre of the aspherical surface of a semi-finished lens blank can therefore be determined as well as a referential as described above.

"inset" is known in the art and may be defined as follows. In a progressive addition lens, the near-vision point (the near-vision point corresponds to the intersection with the gaze direction allowing the wearer to gaze in near-vision, this gaze direction belonging to the meridian line) can be shifted horizontally with respect to a vertical line passing through the distance-vision point, when the lens is in a position of use by its wearer. This shift, which is in the direction of the nasal side of the lens, is referred to as "inset". It generally depends on a number of parameters, such as the optical power of the lens, the distance of observation of an object, the prismatic deviation of the lens and the eye-lens distance, notably. The inset may be an entry parameter selected by an optician at the time of lens order. Inset may be determined by computation or by ray tracing based upon the order data (prescription data).

In the frame of the present invention the average sphere of the front face measured at the prescription point is called a "base-curvature". Depending on the type of lens, the prescription point can be the far vision reference point or the near vision reference point.

The base-curves are usually expressed referring to a standard refractive index of 1.53, whereas other refractive indexes may also be used to refer and express base-curves.

"An optical system" is defined by the coefficients of the equations of all its surfaces, the index of the glasses and the position of each surface relatively to each other (offset, rotation and tilt). These elements are referred as the parameters of the optical system. Surfaces of an optical system are usually represented according to a polynomial or parametric equation obtained by using a model based on the B-splines or Zernike polynomials. These models give continuous curvature on the whole lens. Surfaces can also be Fresnel or pixelized surfaces. The index of materials can be inhomogeneous and depend on some parameters of the optical system.

"Central vision" (also referred as foveal vision) describes the work of the fovea, a small area in the center of the retina that contains a rich collection of cones. In a central vision situation, an observer looks at an object which stays in a gaze direction and the fovea of the observer is moved to follow the object. Central vision permits a person to read, drive, and perform other activities that require fine and sharp vision.

"Pantoscopic angle" of a lens is the angle in the vertical plane between the normal to the front surface of the spectacle lens at its boxed centre and the line of sight of the eye in the primary position, usually taken to be the horizontal.

"Wrap angle" of a lens is the angle in the horizontal plane between the normal to the front surface of the spectacle lens at its boxed centre and the line of sight of the eye in the primary position, usually taken to be straight ahead.

"Peripheral vision" describes the ability to see objects and movement outside of the direct line of vision. In a peripheral vision situation, an observer looks in a fixed gaze direction and an object is seen out of this direct line of vision. The direction of a ray coming from the object to the eye is then different from the gaze direction and is referred as peripheral ray direction. Peripheral vision is the work of the rods, nerve cells located outside the fovea of the retina.

Figure 7:
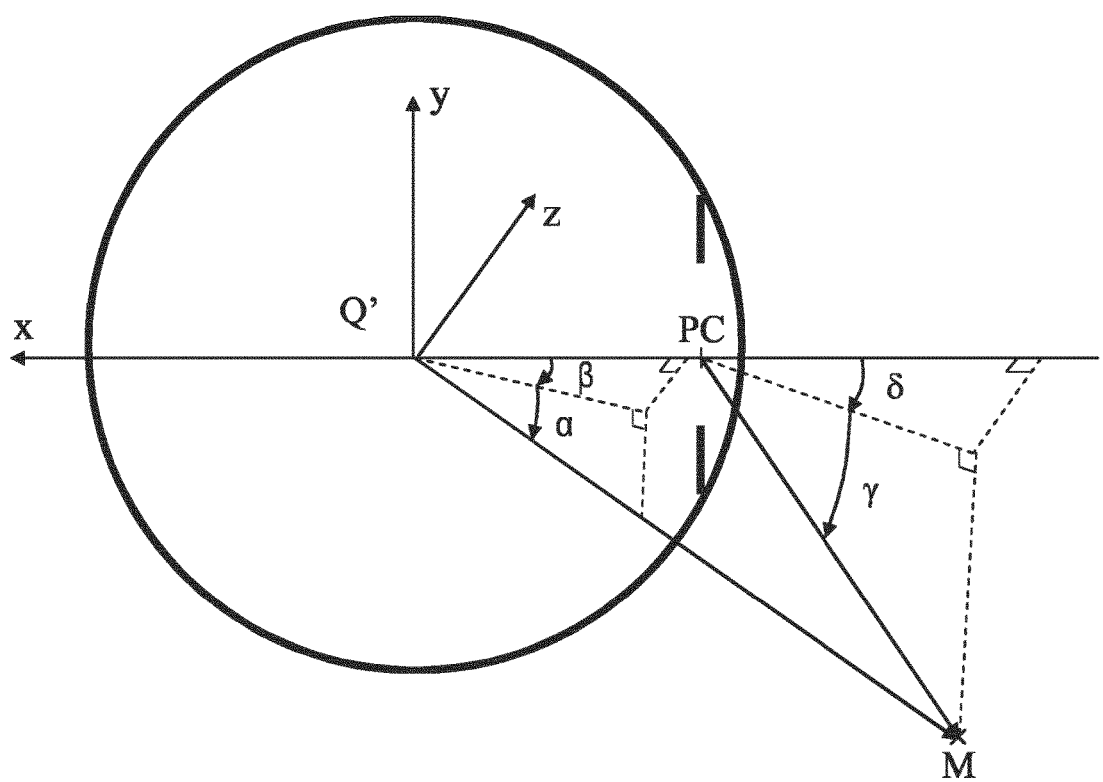
FIG. 7 shows diagrammatically the relationship between the ($\alpha,\beta$) gaze direction and the ($\gamma, \delta$) peripheral ray direction.

As shown in FIG. 7, in the central vision, the couple of angle values ($\alpha,\beta$) are measured with regard to reference axes centered on the center of rotation of the eye Q', whereas in the peripheral vision, the couple of angles value defined as ($\gamma, \delta$) are measured with regard to reference axes centered on the pupil center (PC).

For example, for a given wearer, the distance between Q' and PC is 11.5 mm

"Prismatic deviation" in peripheral vision is defined in the object space by the angular deviation of a ray issued from the center of the entrance pupil introduced by the quantity of prism of the lens Prismatic deviation can be decomposed as the sum of a horizontal deviation dh which is the component along the x-axis, and a vertical deviation dv, which is the component along the y-axis.

"Distortion values" are values related to deviations from rectilinear projection, a projection in which straight lines in a scene remain straight in an image. "Distortions" qualifies the image deformations due to the lens and should be distinguished from aberrations causing image blur such as power error, resulting astigmatism and higher order aberrations. Distortions are considered from the point of view of peripheral vision, i.e. for ray passing through the center of the pupil of the wearer. One can distinguish static distortions, when the gaze direction if fixed, or dynamic distortions, when the gaze direction is changing. Distortions are related to prismatic deviations and their derivatives.

Distortion values can be estimated and/or calculated according to different ways, for example:
- according to the partial derivative of the horizontal prismatic deviation, dha, with respect to gamma angle ($\gamma$) in a ray direction ($\gamma$, $\delta$), and
- according to the partial derivative of the vertical prismatic deviation, dvb, with respect to delta angle ($\delta$) in a ray direction ($\gamma$, $\delta$), with:

$$dha(\gamma, \delta) = \frac{\partial dh((\gamma, \delta))}{\partial \gamma}$$

$$dvb(\gamma, \delta) = \frac{\partial dv((\gamma, \delta))}{\partial \delta}$$

- according to local angular magnification as a function of ray direction ($\gamma$, $\delta$)
- according to the local deformation of a square (as described for example in WO2012119668A1)
- according to the deformation of a line (as described for example in EP1884818A1)
- other distortion criteria known in the art.

In other words, distortion values can be calculated according to one of the here-bellow functions evaluated according to one or a plurality of directions; distortion values can also be calculated according to partial derivatives of said functions evaluated according to one or a plurality of directions; distortion values can also be calculated according to a combination of said functions and/or of the partial derivatives of said functions evaluated according to one or a plurality of directions:

- dh($\alpha$, $\beta$, $\gamma$, $\delta$)=horizontal prismatic deviation of the lens, in degrees, for a given gaze direction ($\alpha$, $\beta$) and a given ray direction ($\gamma$, $\delta$);
- dh(x, y, z, rx, r, $\gamma$, $\delta$)=horizontal prismatic deviation of the lens, in degrees, for a given fixation point (x,y,z), a given head direction (rx,ry) and a given ray direction ($\gamma$, $\delta$);
- dv($\alpha$, $\beta$, $\gamma$, $\delta$)=vertical prismatic deviation of the lens, in degrees, for a given gaze direction ($\alpha$, $\beta$) and a given ray direction ($\gamma$, $\delta$);
- dv(x, y, z, rx, ry, $\gamma$, $\delta$)=vertical prismatic deviation of the lens, in degrees, for a given fixation point (x, y, z), a given head direction (rx, ry) and a given ray direction ($\gamma$, $\delta$);
- m($\alpha$, $\beta$, $\gamma$, $\delta$)=angular magnification of the lens, unit less, for a given gaze direction ($\alpha$, $\beta$) and a given ray direction ($\gamma$, $\delta$);
- m(x, y, z, rx, ry, $\gamma$, $\delta$)=angular magnification of the lens, unit less, for a given fixation point (x, y, z), a given head direction (rx, ry) and a given ray direction ($\gamma$, $\delta$).

Distortion values can also be evaluated as values suitable to measure the deformation of an object seen through the lens. A method of evaluating distortion of a lens may be carried out for example by defining an object geometry (a line, a square, a circle, a grid, a cube, a sphere) in a 3D space then calculating the object deformation in terms of dimensions, aspect ratio, area, volume when this object is seen through the lens.

One can underline that:
- distortions cannot be evaluated in terms of surface characteristics such as sphere, cylinder or cylinder axis;
- distortions cannot be evaluated in terms of wearer power, astigmatism, astigmatism axis, resulting astigmatism, resulting astigmatism axis, acuity or higher order aberrations, which are a measure of image blur and not of image deformation.

According to an embodiment, distortion values are values of a function calculated according to directions, where the function is chosen within the list consisting of: horizontal prismatic deviation of the lens for a given gaze direction and a given ray direction; horizontal prismatic deviation of the lens for a given fixation point, a given head direction and a given ray direction; vertical prismatic deviation of the lens for a given gaze direction and a given ray direction; vertical prismatic deviation of the lens for a given fixation point, a given head direction and a given ray direction; angular magnification of the lens for a given gaze direction and a given ray direction; angular magnification of the lens for a given fixation point, a given head direction and a given ray direction.

According to an embodiment, distortion values are values of partial derivatives of a function calculated according to directions, where the function is chosen within the list consisting of: horizontal prismatic deviation of the lens for a given gaze direction and a given ray direction; horizontal prismatic deviation of the lens for a given fixation point, a given head direction and a given ray direction; vertical prismatic deviation of the lens for a given gaze direction and a given ray direction; vertical prismatic deviation of the lens for a given fixation point, a given head direction and a given ray direction; angular magnification of the lens for a given gaze direction and a given ray direction; angular magnification of the lens for a given fixation point, a given head direction and a given ray direction.

According to an embodiment, distortion values are values of a combination of functions and/or of partial derivatives of said functions calculated according to directions, where the function is chosen within the list consisting of: horizontal prismatic deviation of the lens for a given gaze direction and a given ray direction; horizontal prismatic deviation of the lens for a given fixation point, a given head direction and a given ray direction; vertical prismatic deviation of the lens for a given gaze direction and a given ray direction; vertical prismatic deviation of the lens for a given fixation point, a given head direction and a given ray direction; angular magnification of the lens for a given gaze direction and a given ray direction; angular magnification of the lens for a given fixation point, a given head direction and a given ray direction.

A distortion target (DT) defines, for at least one gaze direction ($\alpha$, $\beta$) and one ray direction ($\gamma$, $\delta$), here above calculated distortion value(s), chosen as the target.

According to an example, a distortion target (DT) is given for the primary gaze direction ($\alpha$, $\beta$)=(0, 0), for an array of ray directions ($\gamma$, $\delta$).

As for an example, one can define a distortion target as follows:
for a single gaze direction ($\alpha$, $\beta$)=(0, 0)
for an array of ray directions:
$\gamma$ from −30 to +30 deg
$\delta$ from −30 to +30 deg specify the values for the following criteria:

$$\frac{\partial dh(\gamma, \delta)}{\partial \gamma}$$

$$\frac{\partial dv(\gamma, \delta)}{\partial \delta}$$

In particular, a distortion target cannot be specified in terms of any of the following criteria:
  surface sphere, surface, cylinder, surface cylinder axis;
  wearer power, astigmatism, astigmatism axis, resulting astigmatism, resulting astigmatism axis, acuity or higher order aberrations Unless specifically stated otherwise, as apparent from the following discussions, it is appreciated that throughout the specification discussions utilizing terms such as "computing", "calculating" "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

DETAILED DESCRIPTION OF THE INVENTION

The invention is illustrated by the following non-limiting example. In all the figures following references are used:
  FVP: far vision point;
  PRP: prism reference point;
  FP: fitting point;
  NVP: near vision point;
  MER: meridian line;
  FVGD: far vision gaze direction;
  NVGD: near vision gaze direction.

In the present example the fitting point, FP, is situated at y=4 mm, on the meridian line.

Example: Calculating a Lens Optical System of a Spectacle Ophthalmic Lens for a Wearer According to the Present Invention This example describes the method for calculating a lens optical system (OS) of a spectacle ophthalmic lens for a wearer according to the invention.
(i) firstly, an aberration target lens (ATL) fulfilling the following requirements is provided:
  The power $PPO_{ATL}$ is −4 Diopter at the the far vision point control point.
  The astigmatism value $AST_{ATL}$ is 0 Diopter and the astigmatism axis $AXE_{ATL}$ is 0° at the far vision control point.
  The addition $Add_{ATL}$ is 2.38 Diopter.
  The base curvature $B_{ATL}$ is 2.77 Diopter.
  The refractive index $n_{ATL}$ is 1.665.
  The distance $d_{ATL}$ is 25.5 mm.
  The wrap angle is 0°.
  The pantoscopic angle is −8°.
(ii) secondly, a distortion target lens (DTL) fulfilling the following requirements is provided:
  The power $PPO_{DTL}$ is −4 Diopter at the far vision control point of the distortion target lens DTL.
  The astigmatism value $AST_{DTL}$ is 0 Diopter and the astigmatism axis $AXE_{ATL}$ is 0° at the far vision point control point distortion target lens DTL.
  The addition $Add_{DTL}$ is 1.79 Diopter.
  The base curvature $B_{DTL}$ is 3.76 Diopter.
  The refractive index $n_{DTL}$ is 1.665.
  The distance $d_{DTL}$ is 25.5 mm.
  The wrap angle is 0°.
  The pantoscopic angle is −8°.

Thus, in this example, the distortion target lens (DTL) comprises target distortion values which are reduced when compared to the distortion values of the aberration target lens (ATL) (reduced addition and enhanced base curvature).

The differences between the distortion targets and the distortion values of the aberration target lens (ATL) are evaluated in terms of mean of the absolute value difference.

The sum is carried over a circular domain having a radius of 60 degrees, with a sampling step of 2 degrees and the circular domain center is (γ, δ)=(10 deg, 0 deg). Following results are obtained:

$$\frac{\sum_{i=1}^{N} |DT(\gamma_i, \delta_i) - dha(ATL, \gamma_i, \delta_i)|}{\sum_{i=1}^{N} |dha(ATL, \gamma_i, \delta_i)|} = 0.165$$

$$\frac{\sum_{i=1}^{N} |DT(\gamma_i, \delta_i) - dvb(ATL, \gamma_i, \delta_i)|}{\sum_{i=1}^{N} |dvb(ATL, \gamma_i, \delta_i)|} = 0.133$$

Figure 8:
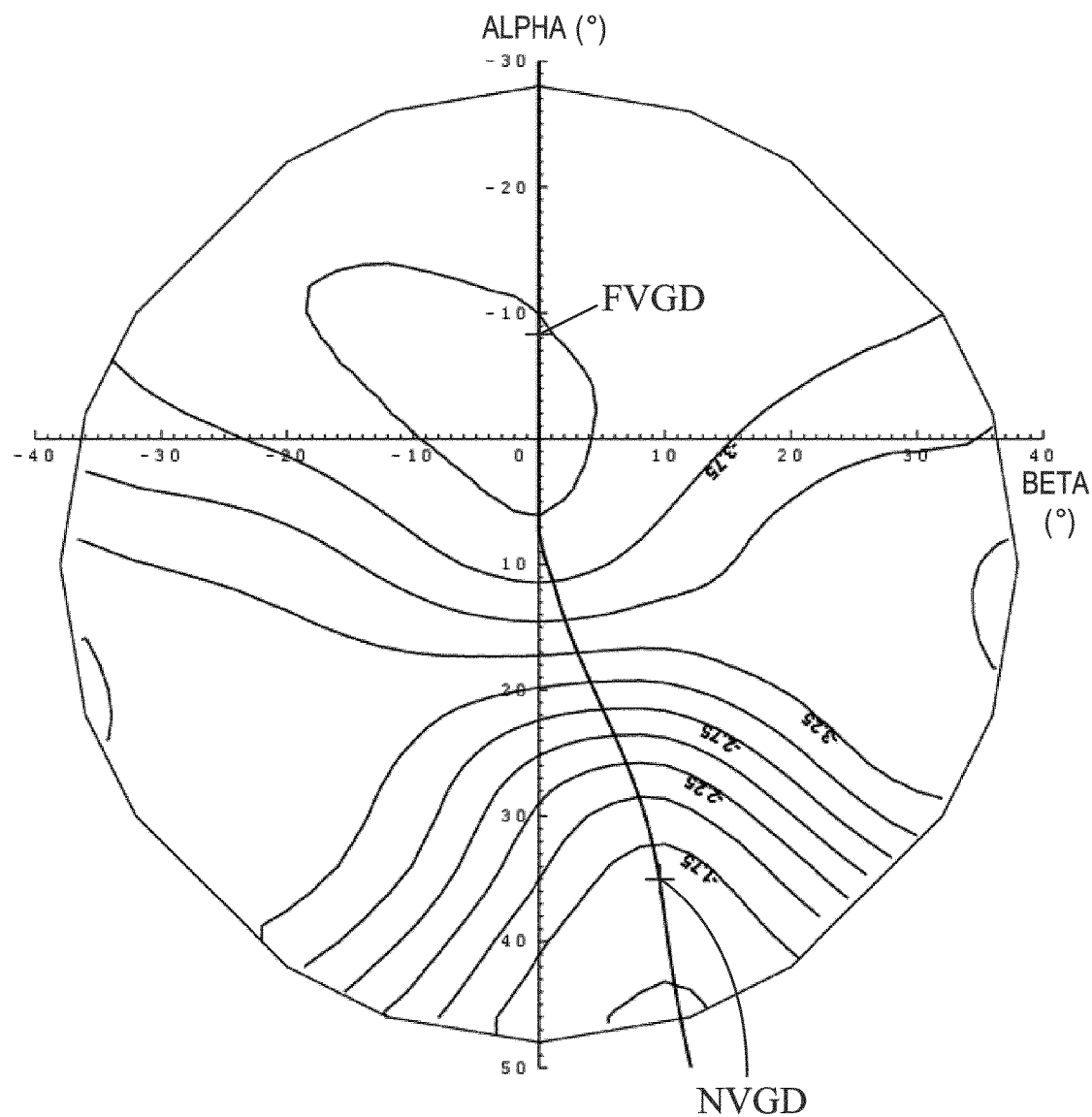
FIGS. 8 to 13 give optical and surface characteristics of an example of a spectacle ophthalmic lens calculated according to the method of the invention.
Figure 9:
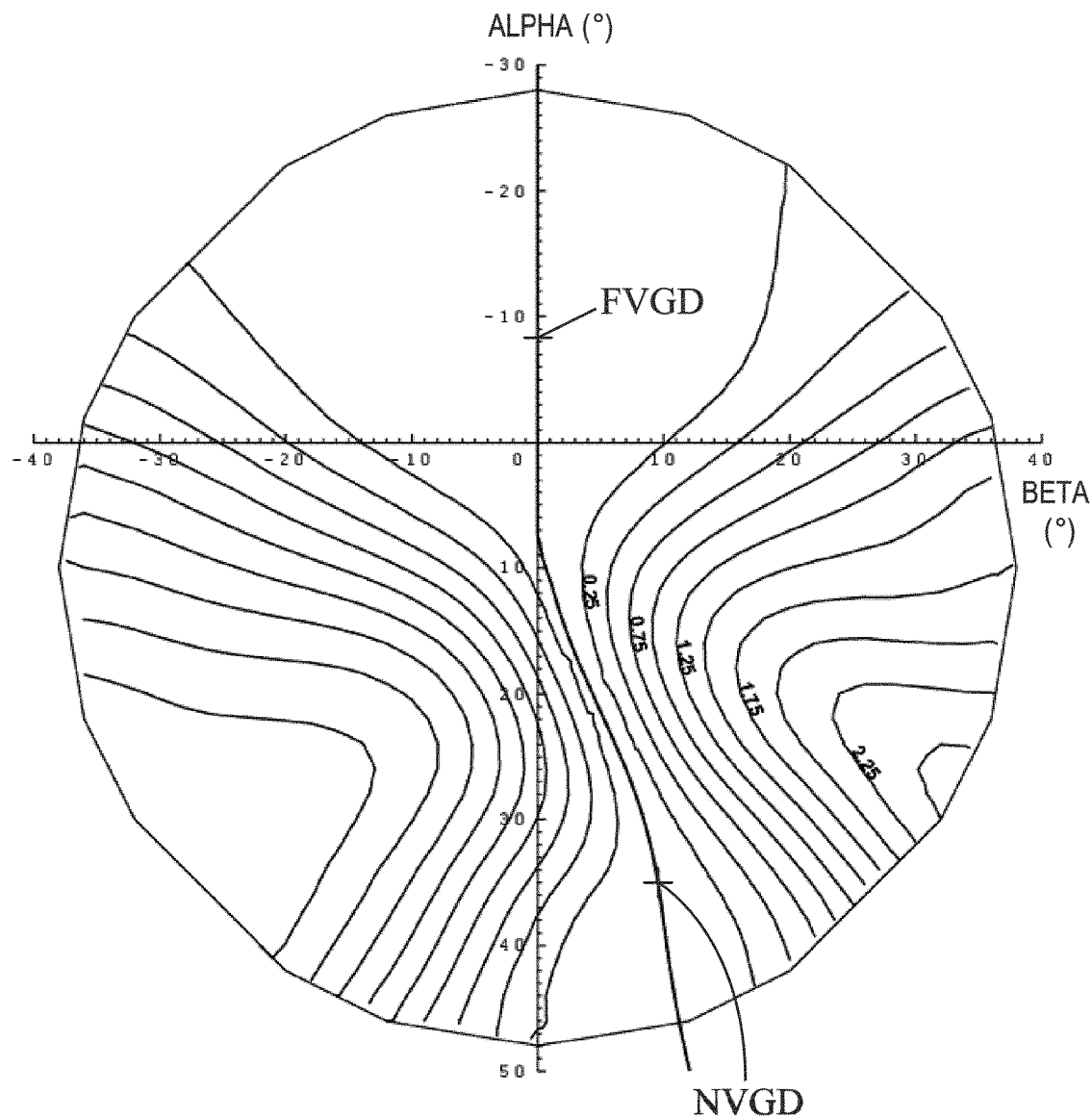

(iii) thirdly, the optimized lens is calculated by using an optimization method which jointly uses the aberration target lens and the target distortion values.
  FIGS. 8 and 9 represent the optical characteristics of the optimized lens calculated in step (iii).

More specifically, FIG. 8 shows the optical power $P_{opt}(\alpha, \beta)$ iso-lines (0.25 Diopter between two neighbouring lines), according to the ($\alpha$, $\beta$) referential of the lens.

FIG. 9 shows the resulting astigmatism iso-lines (0.25 Diopter between two neighbouring lines), according to the ($\alpha$, $\beta$) referential of the lens.

The following table 1 represents:
- the difference between the optical power $PPO_{opt}(\alpha, \beta)$ of the optimized lens and the optical power $PPO_{ATL}(\alpha, \beta)$ of the aberration target lens (ATL), and
- the difference between the resulting astigmatism $ASR_{opt}(\alpha, \beta)$ of the optimized lens and the resulting astigmatism $ASR_{ATL}(\alpha, \beta)$ of the aberration target lens (ATL)

The evaluations are carried over a circular domain having a radius of 38 degrees, with a sampling step of 2 degrees and the circular domain center is ($\alpha$, $\beta$)=(10 deg, 0 deg).

TABLE 1 optical characteristics differences between the optimized lens and the aberration target lens (ATL).

| | optical power difference (Diopter) optimized lens − aberration target lens (ATL) | resulting astigmatism difference (Diopter) optimized lens − aberration target lens (ATL) |
|---|---|---|
| Mean (Diopters) | −0.001 | 0.001 |
| Rms (root mean square) (Diopters) | 0.003 | 0.005 |
| Min (Diopters) | −0.031 | −0.048 |
| Max (Diopters) | 0.020 | 0.041 |

As shown in table 1, the optical characteristics (optical power and resulting astigmatism) differences between the aberration target lens (ATL) and the optimized lens are negligible. In other terms:
- the optical power $PPO_{ATL}(\alpha, \beta)$ iso-lines of the aberration target lens (ATL) (not shown in this example) and the optical power $PPO_{opt}(\alpha, \beta)$ iso-lines of the optimized lens are well superimposed, and
- the resulting astigmatism $ASR_{ATL}(\alpha, \beta)$ iso-lines of the aberration target lens (ATL) (not shown in this example) and the resulting astigmatism $ASR_{opt}(\alpha, \beta)$ iso-lines of the optimized lens are well superimposed.

Thus, the optimized lens has the optical characteristics of the aberration target lens (ATL).

In a same way, the following table 2 represents:
- the difference between dha of the optimized lens and the dha of the distortion target lens (DTL), and
- the difference between dvb of the optimized lens and the dvb of the distortion target lens (DTL).

The evaluations are carried over a circular domain having a radius of 60 degrees, with a sampling step of 2 degrees and the circular domain is centered in ($\gamma$, $\delta$)=(10 deg, 0 deg).

TABLE 2 distortion characteristics differences between the optimized lens and the distortion target lens (DTL).

| | dha difference optimized lens − distortion target lens (DTL) | dvb difference optimized lens − distortion target lens (DTL) |
|---|---|---|
| Mean (dimensionless) | 0.000 | 0.000 |
| Rms (root mean square) (dimensionless) | 0.001 | 0.001 |
| Min (dimensionless) | −0.001 | −0.005 |
| Max (dimensionless) | 0.003 | 0.003 |

As shown in table 2, the distortion characteristics (dha and dvb) differences between the distortion target lens (DTL) and the optimized lens are negligible. In other terms:
- the dha iso-lines of the distortion target lens (DTL) (not shown in this example) and the dha iso-lines of the optimized lens are well superimposed, and
- the dvb iso-lines of the distortion target lens (DTL) (not shown in this example) and the dvb iso-lines of the optimized lens are well superimposed.

Thus, the optimized lens has the distortion characteristics of the distortion target lens (DTL).

In this example, both of the front surface and back surface of the spectacle ophthalmic lens were optimized.

The optimization method used in this example is the method disclosed in the patent application WO2010/043704.

According to this example, the initial lens for the optimization procedure is chosen in order to perform more quickly the optimization process. For example, the initial lens is determined so as to have parameters intermediate between the aberration target lens (ATL) and the distortion target lens (DTL). In this case, the starting lens has the following parameters:
- The power PPO is −4 Diopter at the far vision point control point.
- The astigmatism value AST is 0 Diopter and the axis AXE is 0° at the far vision control point.
- The addition Add is 2.09 Diopter.

Alternatively, the initial lens used for optimization may also be the aberration target lens (ATL)

FIGS. 10-13 represent the surface characteristics of the optimized lens calculated in step (iii).

Figure 10:
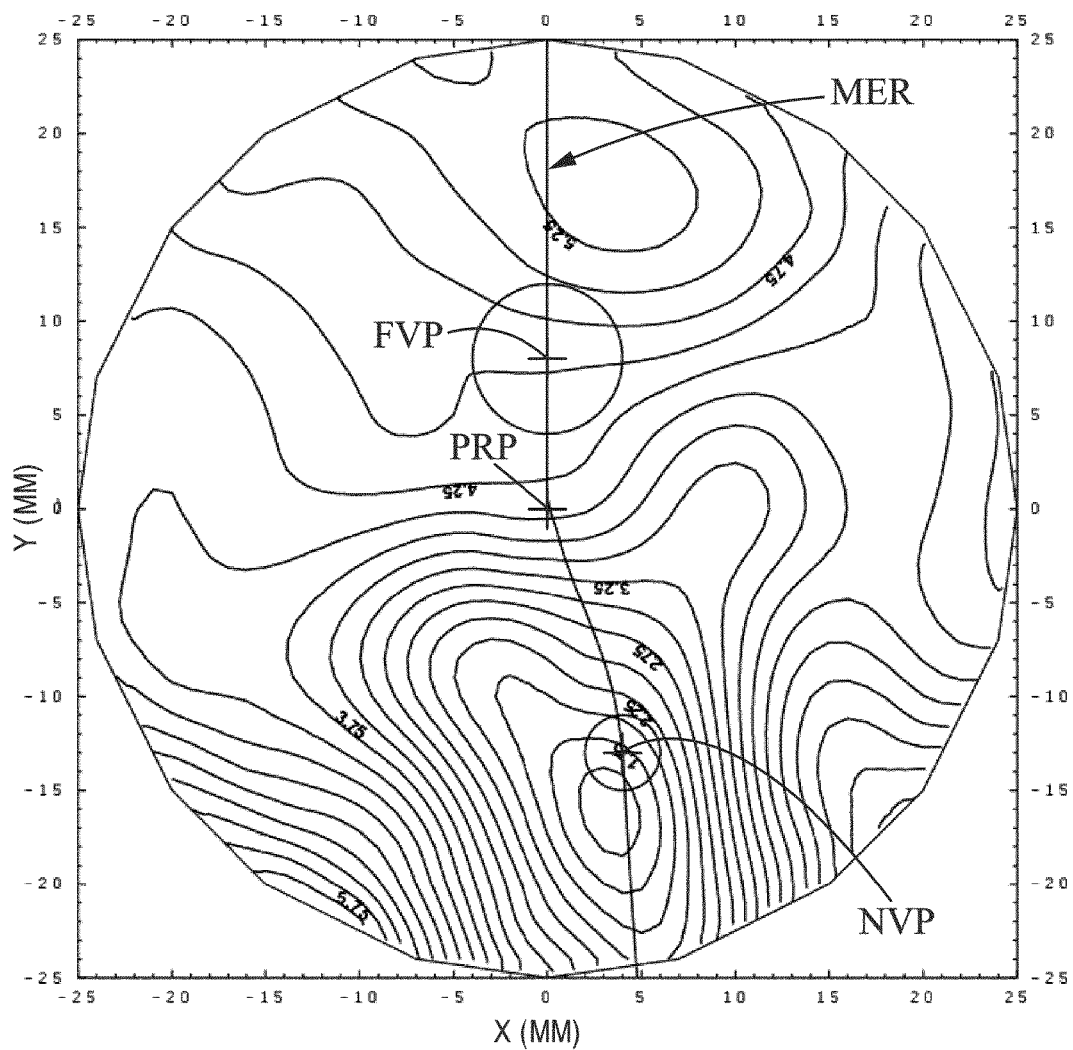
Figure 11:
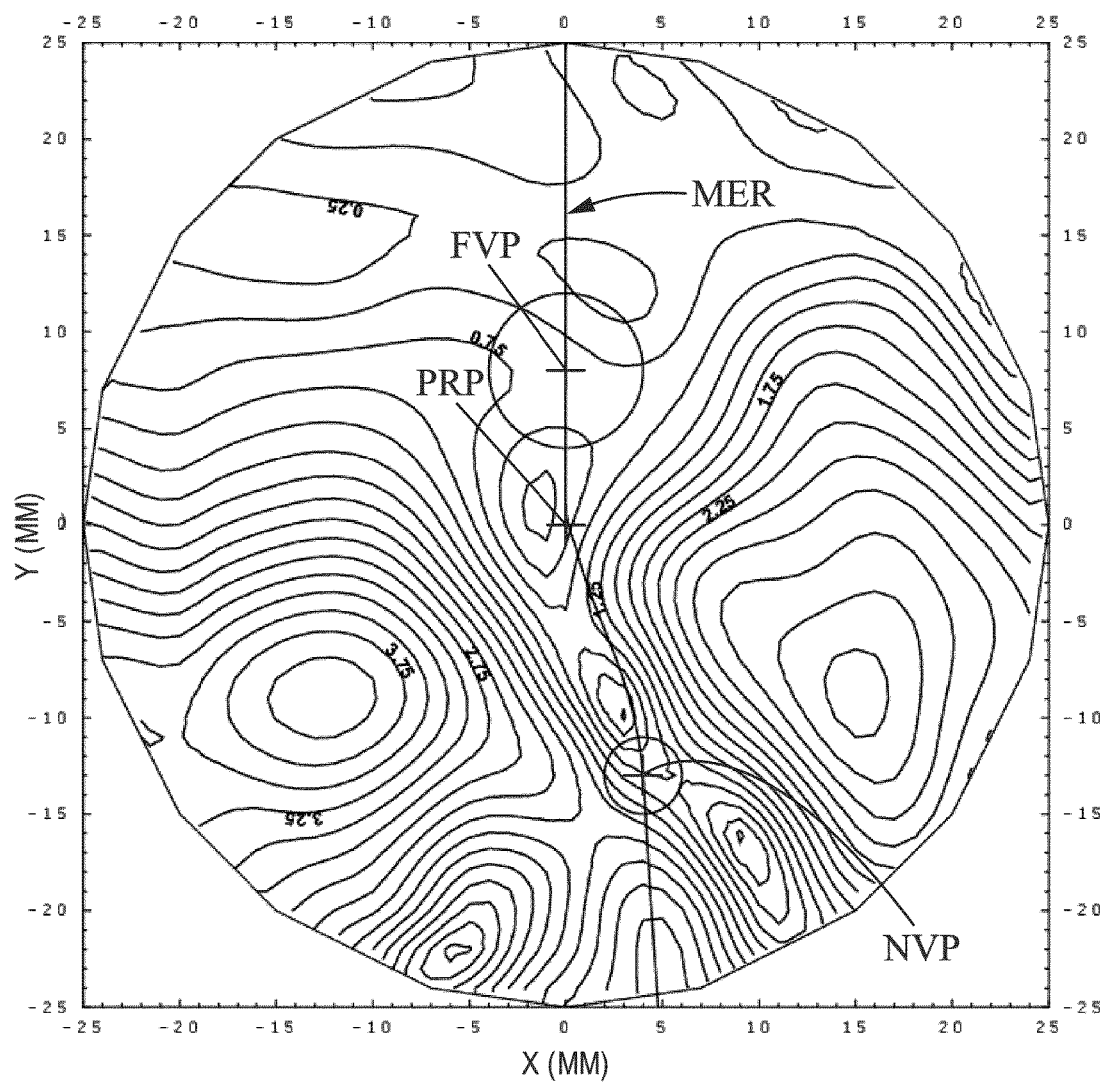

More specifically, FIG. 10 shows the mean sphere iso-lines (0.25 Diopter between two neighbouring lines) on the front surface of the lens, according to the (x,y) referential of the front surface;

FIG. 11 shows the cylinder iso-lines (0.25 Diopter between two neighbouring lines) on the front surface of the lens, according to the (x,y) referential of the front surface.

Figure 12:
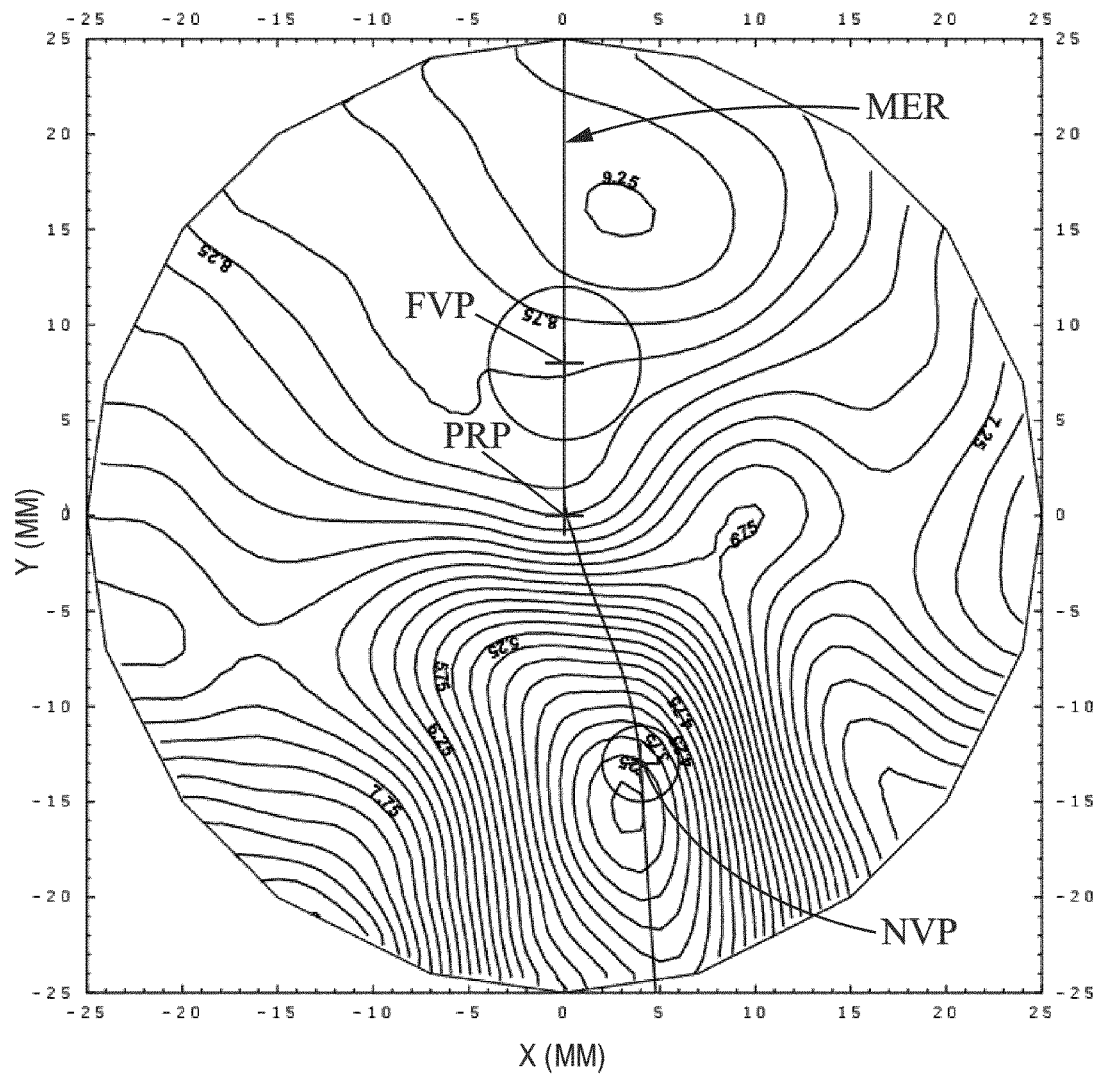
Figure 13:
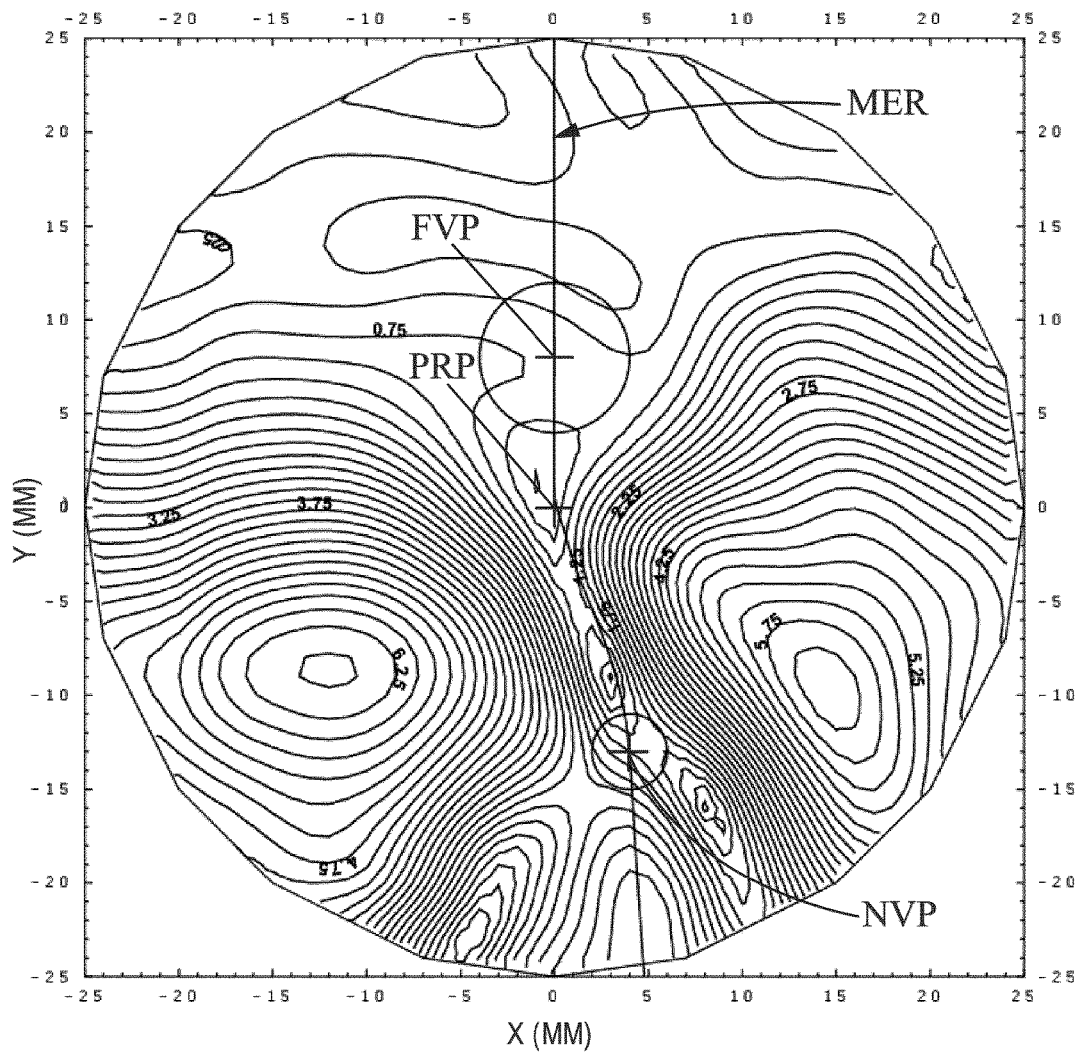

FIG. 12 shows the mean sphere iso-lines (0.25 Diopter between two neighbouring lines) on the back surface of the lens, according to the (x,y) referential of the back surface;

FIG. 13 shows the cylinder iso-lines (0.25 Diopter between two neighbouring lines) on the back surface of the lens, according to the (x,y) referential of the back surface.

Figure 14:
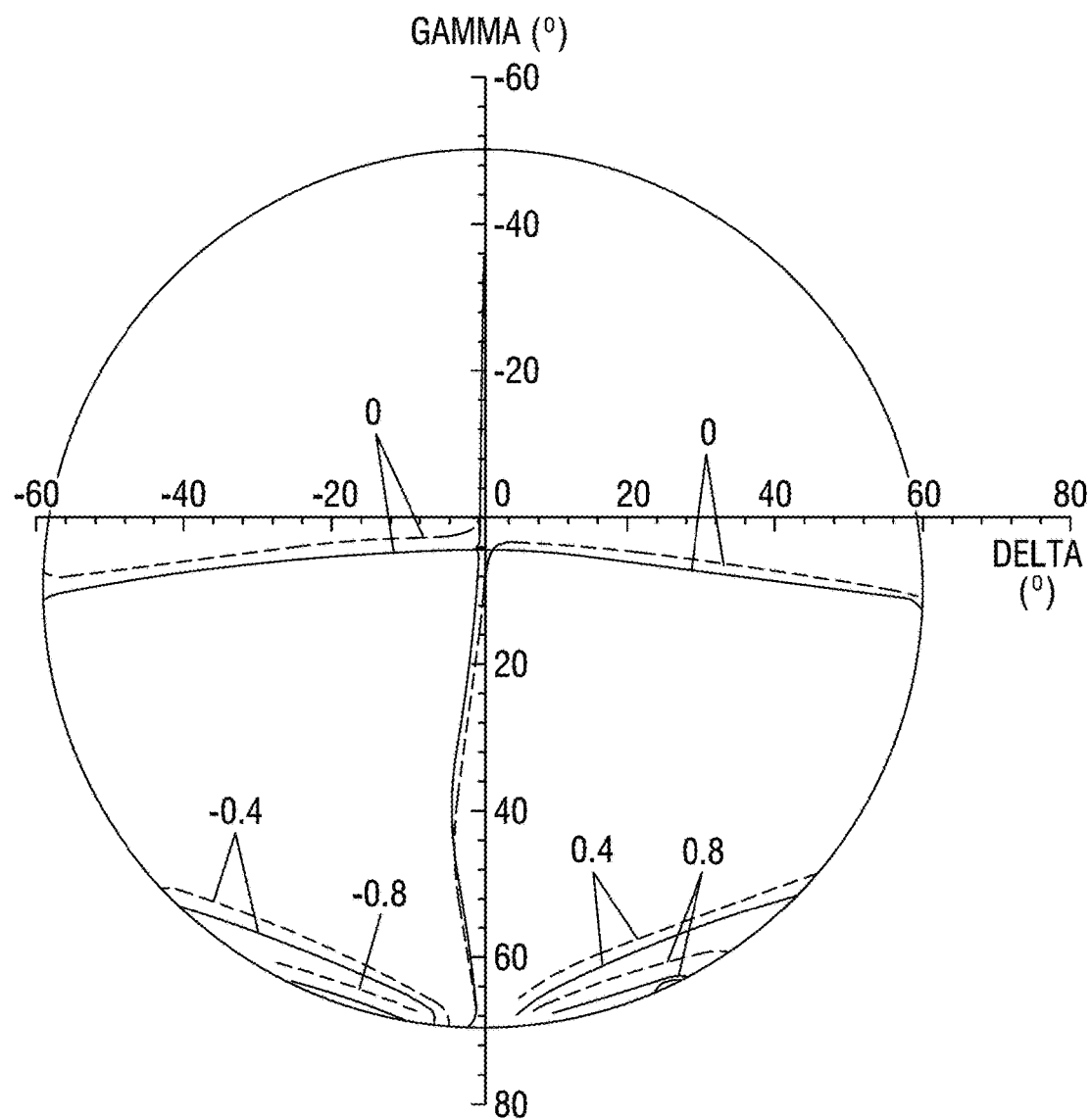
FIGS. 14 and 15 give distortion characteristics of an example of a spectacle ophthalmic lens calculated according to the method of the invention.
Figure 15:
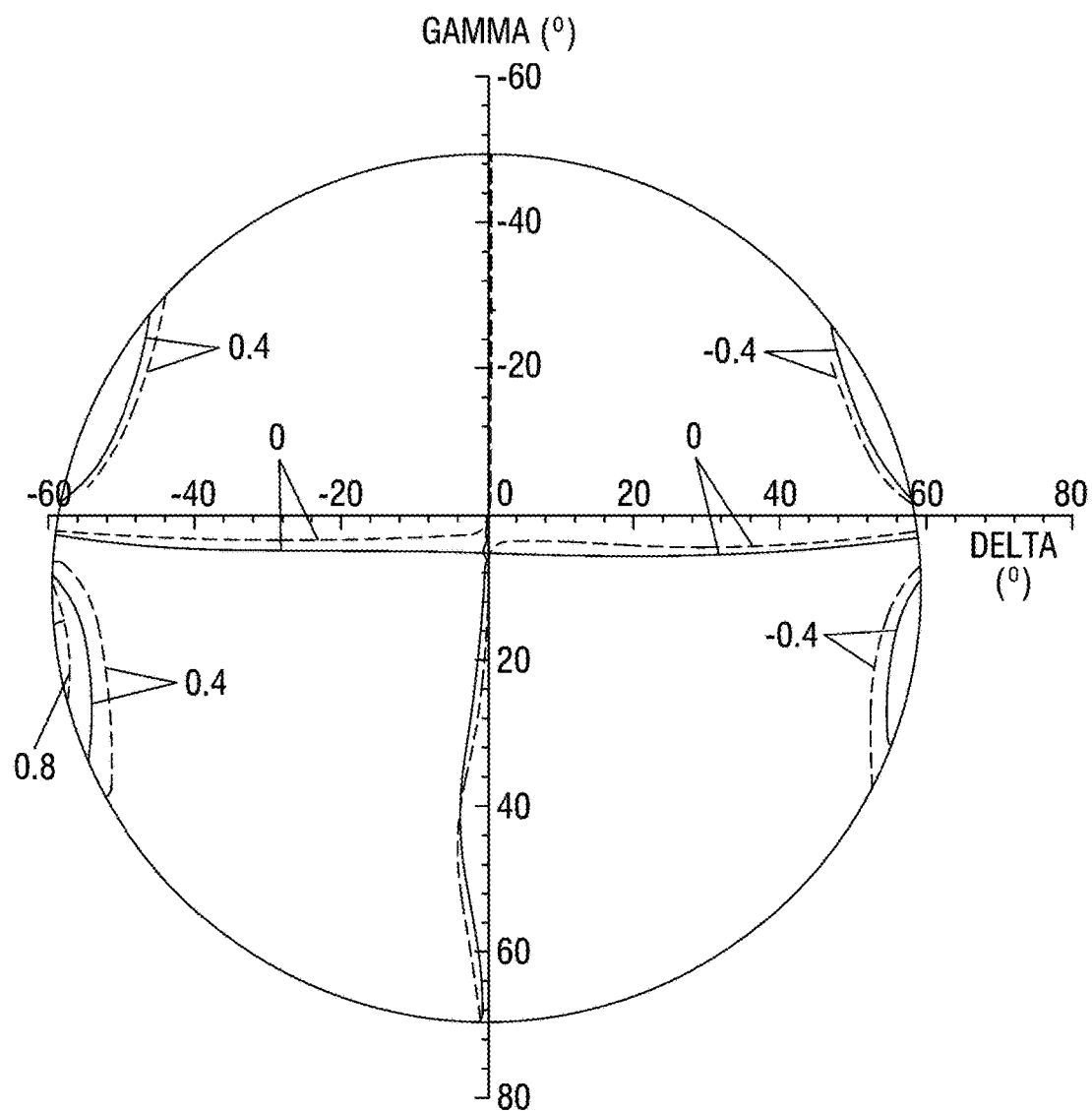

FIGS. 14 and 15 represent the distortion characteristics (dha for FIG. 14 and dvb for FIG. 15) comparison between the aberration target lens (ATL) (represented with dashed lines in FIGS. 14 and 15) and the optimized lens (represented with solid lines in FIGS. 14 and 15) according to the ($\gamma$, $\delta$) referential of the lens.

It can be seen from these figures that the distortions of the optimized lens are reduced when compared to the distortions of the aberration target lens (ATL). In the present example, the optimized lens has the distortions equivalent to the distortions of a lens having a reduced addition.

Thus, the method of the invention enables one to provide a spectacle ophthalmic lens having reduced distortions while meeting the requirements of the aberration target lens.

Furthermore, the inventors have developed a method that is suitable to determine whether a manufactured spectacle ophthalmic lens results from the method for calculating a lens optical system (OS) according to the present invention.

A manufactured spectacle ophthalmic lens is provided with the prescription data (Rx0) for which said lens has been manufactured.

According to following example, the manufactured spectacle ophthalmic lens is a progressive addition lens.

Said manufactured spectacle ophthalmic lens is measured so as to determine the geometry of its front and back surfaces; surface metrology of spectacle ophthalmic lens is known for a person skilled in the art.

Wearing conditions are provided comprising at least a distance between the center of rotation of the eye of the wearer and the back surface of the lens, a pantoscopic angle and a wrap angle. For example one can use the following values:
- distance between the center of rotation of the eye of the wearer and the back surface of the lens is 25.5 mm
- pantoscopic angle is 8 degrees
- wrap angle is 0 degrees One defines an evaluation domain, Dab, where $\alpha$ is within the range [−30 degree, 40 degree], $\beta$ is within the range [−40 degree, 40 degree].

Thanks to these data, one can calculate aberrations of the said manufactured spectacle ophthalmic lens so as to determine $PPO_m(\alpha, \beta)$, $ASR_m(\alpha, \beta)$ according to the gaze directions in the evaluation domain Dab.

One defines parameters of a first target lens, Vc1 as follows:
- refractive index of the first target lens is the one of the manufactured spectacle ophthalmic lens;
- front curvature of the first target lens is the value of the Tscherning curvature in acuity calculated for the prescription data corresponding to Rx0;
- the distance between the center of rotation of the eye of the wearer and the back surface of the first target lens lens is $d_{VC1}$=25.5 mm;
- prescription data of the first target lens Rx1 corresponds to Rx0:
- the thickness of the first target lens is 3 mm at the center and 1 mm at the points of a centered circle of 35 mm diameter;
- the back surface of the first target lens is a spherical surface.

Using said data, one calculates the front and back surfaces of the first target lens, Vc1, so as the aberrations are $PPO_m(\alpha, \beta)$, $ASR_m(\alpha, \beta)$ over the evaluation domain Dab.

One provides an addition reduction value; according to an embodiment, the addition reduction value is equal to 0.5 Diopter.

One provides a second target lens Vc2, where its front surface is calculated from the front surface of the first target lens Vc1 so as to obtain an addition that is reduced from the addition reduction value and where said second target lens is determined thanks to following input data:
- refractive index of the second target lens is the one of the manufactured spectacle ophthalmic lens;
- front surface is the calculated front surface of the second target lens Vc2;
- prescription data of the second target lens Rx2 corresponds to Rx0;
- the distance between the center of rotation of the eye of the wearer and the back surface of the second target lens is $d_{VC2}$=25.5 mm
- the thickness of the second target lens is 3 mm at the center and 1 mm at the points of a centered circle of 35 mm diameter;
- the back surface of the second target lens is a torical surface.

The back surface of the second target lens Vc2 is then calculated so as to obtain the required prescription in terms of Sphere, Cylinder and Axis.

One calculates the partial derivative of the horizontal prismatic deviation, dha, with respect to gamma angle ($\gamma$) in a ray direction ($\gamma$, $\delta$), and the partial derivative of the vertical prismatic deviation, dvb, with respect to delta angle ($\delta$) in a ray direction ($\gamma$, $\delta$), for both the manufactured spectacle ophthalmic lens and the second target lens Vc2.

Based on these data, one calculates the global lens distortions, $DIST_m$ and $DIST_{c2}$, of respectively the manufactured spectacle ophthalmic lens and the second target lens Vc2. The global lens distortion can be defined as the sum of dha and dvb. It can be evaluated for all points of a circular domain of radius 50 degrees centered in ($\gamma$, $\delta$)=(10 deg, 0 deg).

Said global lens distortions, $DIST_m$ and $DIST_{c2}$ are compared and if the requirements of following equation are fulfilled, $$RMS((DIST_{c2}-DIST_m)/DIST_m)<5\%,$$

one demonstrates that the optical system of the manufactured spectacle ophthalmic lens should have been determined according to the teaching of the present invention.

The invention claimed is:

1. A method of manufacturing a spectacle ophthalmic lens by machining a lens blank according to a lens optical system, the lens optical system calculated with a method implemented by computer means for calculating the lens optical system of the spectacle ophthalmic lens for a wearer where the spectacle ophthalmic lens comprises a back surface and a front surface, the back surface being positioned closest to the wearer's eye when the spectacle ophthalmic lens is worn, the method implemented by the computer means comprising:
   providing an aberration target lens comprising a back surface and a front surface, said aberration target lens having distortion values and fulfilling the requirements of:
      a first set of aberration data of the aberration target lens including at least an aberration datum at a point of said aberration target lens chosen within the list consisting of a power $PPO_{ATL}$, an astigmatism amplitude value $AST_{ATL}$ with an astigmatism axis $AXE_{ATL}$, and an addition $Add_{ATL}$,
      a first set of wearing parameters of the aberration target lens, and
      a first set of lens parameters of the aberration target lens;
   providing a distortion target consisting of target distortion values wherein $$\frac{\sum_{i=1}^{N} |DT(\gamma_i, \delta_i) - Dist(ATL, \gamma_i, \delta_i)|}{\sum_{i=1}^{N} |Dist(ATL, \gamma_i, \delta_i)|} \geq Q$$

where:
- DT is a distortion target value of the distortion target;
- $(\gamma_i, \delta_i)$ is a mesh of a distortion zone;
- N is the number of points in the mesh:
- Dist is the distortion criterion;
- ATL is the aberration target lens; and
- Q=5%; and calculating the lens optical system by using an optimization method which jointly uses the aberration target lens and the target distortion values, wherein said first set of wearing parameters of the aberration target lens includes a first distance, $d_{ATL}$, between the center of rotation of the eye of the wearer and the back surface of said aberration target lens, said first set of lens parameters of the aberration target lens includes a first refractive index, $n_{ATL}$ of said aberration target lens, a first base curvature, $B_{ATL}$, being the curvature on a reference point of the front surface of the aberration target lens, wherein the distortion target is a distortion target lens, wherein said distortion target lens is provided with a second set of aberration data, a second set of wearing parameters including a second distance, $d_{DTL}$, between a center of rotation of the eye of the wearer and the back surface of said distortion target lens, and a second set of lens parameters including a second refractive index, $n_{DTL}$ of said distortion target lens and a second base curvature, $B_{DTL}$, and wherein the first and the second set of aberration data differ from at least data value and/or the first and the second set of wearing parameters differ from at least one wearing parameter value and/or the first and the second set of lens parameters differ from at least one lens parameter value.

2. The method of claim 1, wherein Q=10%.

3. The method according to claim 1, wherein:
the spectacle ophthalmic lens is a single vision ophthalmic lens,
the first set of aberration data comprises at least a value chosen within the list consisting of a power $PPO_{ATL}$, an astigmatism amplitude $AST_{ATL}$ with an astigmatism axis value $AXE_{ATL}$ with the proviso that addition $Add_{ATL}$ is nil, and
the second set of aberration data comprises at least a value chosen within the list consisting of a power $PPO_{DTL}=PPO_{ATL}-\Delta PPO$ at a point of said distortion target lens, an astigmatism amplitude $AST_{DTL}=AST_{ATL}-\Delta AST$ at a point of said distortion target lens with an astigmatism axis value $AXE_{DTL}$, where $\Delta PPO$ and/or $\Delta AST$ is not nil.

4. The method according to claim 3, wherein:
$\Delta PPO$ is of the same sign as $PPO_{ATL}$ and satisfies the equation:

0.25 Diopter<|ΔPPO|≤2.0 Diopter, and/or $\Delta AST$ is of the same sign as $AST_{ATL}$ and satisfies the equation:

0.25 Diopter <|ΔAST|≤2.0 Diopter.

5. The method according to claim 1, wherein the spectacle ophthalmic lens is a progressive addition lens chosen within the list consisting of a lens comprising a far vision zone, an intermediate vision zone and a near vision zone; a lens comprising an intermediate vision zone and a near vision zone; a lens comprising a far vision zone and an intermediate vision zone, wherein
the first set of aberration data comprises at least a power value $PPO_{ATL}$, a non-nil addition $Add_{ATL}$ and optionally a astigmatism amplitude value $AST_{ATL}$ with an astigmatism axis value $AXE_{ATL}$, and
the second set of aberration data comprises at least a value chosen within the list consisting of a power $PPO_{DTL}=PPO_{ATL}-\Delta PPO$, an addition $Add_{DTL}=Add_{ATL}-\Delta Add$ and optionally an astigmatism amplitude value $AST_{DTL}=AST_{ATL}-\Delta AST$ with an astigmatism axis value $AXE_{DTL}$, where $\Delta PPO$ and/or $\Delta AST$ and/or $\Delta Add$ is not nil.

6. The method according to claim 5, wherein:
$\Delta Add$ is positive and satisfies the equation:

0.125 Diopter≤ΔAdd≤1.5 Diopter, and/or $\Delta PPO$ is of the same sign as $PPO_{ATL}$ and satisfies the equation:

0.25 Diopter≤|ΔPPO|≤2.0 Diopter and/or
$\Delta AST$ is of the same sign as $AST_{ATL}$ and satisfies the equation:

0.25 Diopter≤|ΔAST|≤2.0 Diopter.

7. The method according to claim 1, wherein the second refractive index $n_{DTL}$ differs from the first refractive index, $n_{ATL}$.

8. The method according to claim 1, wherein the second distance, $d_{DTL}$, differs from the first distance, $d_{ATL}$.

9. The method of claim 8, wherein $d_{ATL}-d_{DTL}\geq 1$ mm.

10. The method according to claim 1, wherein the second base curvature, $B_{DTL}$, differs from said first base curvature, $B_{ATL}$.

11. The method according to claim 10, wherein $B_{DTL}-B_{ATL}\geq 1$ Diopter.

12. A non-transitory computer program product comprising one or more stored sequence of instruction that is accessible to a processor and which, when executed by the processor, causes the processor to carry out at least the steps of claim 1.

13. A non-transitory computer readable medium carrying one or more sequences of instructions of the computer program product of claim 12.

* * * * *